(12) United States Patent
Bosua

(10) Patent No.: US 11,696,698 B1
(45) Date of Patent: Jul. 11, 2023

(54) ANALYTE SENSORS WITH POSITION ADJUSTABLE TRANSMIT AND/OR RECEIVE COMPONENTS

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 17/937,542

(22) Filed: Oct. 3, 2022

(51) Int. Cl.
| | | |
|---|---|---|
| G01S 17/34 | (2020.01) | |
| A61B 5/00 | (2006.01) | |
| G01S 17/89 | (2020.01) | |
| G01N 21/39 | (2006.01) | |
| A61B 5/0507 | (2021.01) | |
| G01N 27/327 | (2006.01) | |
| A61B 5/145 | (2006.01) | |

(52) U.S. Cl.
CPC .......... *A61B 5/0507* (2013.01); *A61B 5/0075* (2013.01); *A61B 5/14546* (2013.01); *G01N 27/3273* (2013.01)

(58) Field of Classification Search
CPC . A61B 5/0507; A61B 5/0075; A61B 5/14546; G01N 27/3273
See application file for complete search history.

(56) References Cited

U.S. PATENT DOCUMENTS

| | | | |
|---|---|---|---|
| 4,202,000 | A | 5/1980 | Carballes |
| 6,762,867 | B2 | 7/2004 | Lippert et al. |
| 8,223,021 | B2 | 7/2012 | Goodnow et al. |
| 8,882,670 | B2 | 11/2014 | Hancock |
| 9,198,607 | B2 | 12/2015 | Fischer |
| 9,625,371 | B2 | 4/2017 | Furness, III et al. |
| 9,664,610 | B2 | 5/2017 | Wander et al. |

(Continued)

FOREIGN PATENT DOCUMENTS

| | | |
|---|---|---|
| EP | 3146898 B1 | 11/2018 |
| EP | 3981329 | 4/2022 |

(Continued)

OTHER PUBLICATIONS

U.S. Appl. No. 17/937,540, titled "Analyte Sensors With Position Adjustable Transmit and/or Receive Components," filed Oct. 3, 2022 (42 pages).

(Continued)

*Primary Examiner* — Giovanni Astacio-Oquendo
*Assistant Examiner* — Zannatul Ferdous
(74) *Attorney, Agent, or Firm* — Hamre, Schumann, Mueller & Larson, P.C.

(57) ABSTRACT

An analyte sensor that detects an analyte via spectroscopic techniques using frequencies in the radio or microwave frequency range of the electromagnetic spectrum. The analyte sensor is configured to permit adjustment of the position(s) of one or more transmit components and/or the position(s) of one or more receive components. Adjusting position (or the like) as used in the description and claims includes changing an angle of the transmit component(s) and/or the receive component(s), and/or moving the transmit component(s) and/or the receive component(s) in one or more X, Y, Z directions, and/or changing a shape of the transmit component(s) and/or the receive component(s), and any combinations thereof.

27 Claims, 11 Drawing Sheets

(56) References Cited

U.S. PATENT DOCUMENTS

| | | |
|---|---|---|
| 9,864,024 B2 | 1/2018 | Vester |
| 10,149,629 B2 | 12/2018 | Szczepaniak et al. |
| 10,258,268 B2 | 4/2019 | Roblyer et al. |
| 10,478,101 B1 | 11/2019 | Cespedes et al. |
| 10,548,503 B2 | 2/2020 | Bosua |
| 10,617,296 B2 | 4/2020 | Sloan et al. |
| 10,856,766 B2 | 12/2020 | Leabman |
| 10,912,500 B2 | 2/2021 | Poeze et al. |
| 10,956,950 B2 | 3/2021 | Al-Ali et al. |
| 11,031,970 B1 | 6/2021 | Bosua |
| 11,033,208 B1 | 6/2021 | Bosua |
| 11,058,317 B1 | 7/2021 | Bosua |
| 11,058,331 B1 | 7/2021 | Bosua |
| 11,063,373 B1 | 7/2021 | Bosua |
| 11,193,923 B2 | 12/2021 | Bosua |
| 11,202,582 B2 | 12/2021 | Verkruijsse et al. |
| 11,223,383 B2 | 1/2022 | Bosua |
| 11,234,618 B1 | 2/2022 | Bosua et al. |
| 11,234,619 B2 | 2/2022 | Bosua |
| 11,244,753 B2 | 2/2022 | Haggerty et al. |
| 11,284,819 B1 | 3/2022 | Bosua et al. |
| 11,284,820 B1 | 3/2022 | Bosua et al. |
| 11,291,374 B2 | 4/2022 | Lee et al. |
| 11,298,037 B2 | 4/2022 | Leabman |
| 11,350,830 B2 | 6/2022 | McKenna et al. |
| 11,360,188 B2 | 6/2022 | Leabman |
| 11,367,525 B2 | 6/2022 | Addison et al. |
| 11,389,091 B2 | 7/2022 | Bosua |
| 11,389,093 B2 | 7/2022 | Triman et al. |
| 11,426,104 B2 | 8/2022 | Schurman et al. |
| 2003/0036713 A1 | 2/2003 | Bouton et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2008/0319285 A1 | 12/2008 | Hancock |
| 2009/0112101 A1 | 4/2009 | Furness, III et al. |
| 2009/0275814 A1 | 11/2009 | Watanabe et al. |
| 2010/0041969 A1 | 2/2010 | Beise |
| 2011/0028814 A1 | 2/2011 | Petersen et al. |
| 2013/0289375 A1 | 10/2013 | Fischer |
| 2014/0213870 A1 | 7/2014 | Hsu et al. |
| 2016/0051171 A1 | 2/2016 | Pikov et al. |
| 2017/0095667 A1 | 4/2017 | Yakovlev et al. |
| 2017/0164878 A1 | 6/2017 | Connor |
| 2018/0028824 A1 | 2/2018 | Pivonka et al. |
| 2018/0303391 A1 | 10/2018 | Roblyer et al. |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0269853 A1 | 9/2019 | Doyle et al. |
| 2019/0388000 A1 | 12/2019 | Costantine et al. |
| 2020/0054255 A1 | 2/2020 | Conrad et al. |
| 2020/0057163 A1 | 2/2020 | Bromberg |
| 2020/0146584 A1 | 5/2020 | Bosua |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2021/0063366 A1* | 3/2021 | Potyrailo ............ G01N 33/0031 |
| 2021/0186357 A1 | 6/2021 | Bosua et al. |
| 2021/0244308 A1 | 8/2021 | Bosua |
| 2021/0259571 A1 | 8/2021 | Bosua |
| 2021/0259592 A1 | 8/2021 | Bosua |
| 2021/0259593 A1 | 8/2021 | Bosua |
| 2021/0307660 A1* | 10/2021 | Chauhan ................ A61B 5/097 |
| 2022/0015695 A1 | 1/2022 | Margarito et al. |
| 2022/0031254 A1 | 2/2022 | Al-Ali et al. |
| 2022/0071505 A1 | 3/2022 | Bosua |
| 2022/0071523 A1 | 3/2022 | Bosua |
| 2022/0071524 A1 | 3/2022 | Bosua |
| 2022/0071527 A1 | 3/2022 | Bosua |
| 2022/0074870 A1 | 3/2022 | Bosua |
| 2022/0074871 A1 | 3/2022 | Bosua |
| 2022/0077602 A1 | 3/2022 | Bosua et al. |
| 2022/0077918 A1 | 3/2022 | Bosua et al. |
| 2022/0151553 A1 | 5/2022 | Bosua |
| 2022/0192494 A1 | 6/2022 | Leabman |
| 2022/0192531 A1 | 6/2022 | Leabman |
| 2022/0225899 A1* | 7/2022 | Peterson .............. A61B 5/6848 |
| 2022/0248984 A1 | 8/2022 | Poeze et al. |
| 2022/0413143 A1 | 12/2022 | Parsa et al. |

FOREIGN PATENT DOCUMENTS

| | | |
|---|---|---|
| JP | 2012125382 | 7/2012 |
| KR | 1020160081740 | 7/2016 |
| WO | 2017163245 | 9/2017 |
| WO | 2019071138 | 4/2019 |
| WO | 2019217461 | 11/2019 |
| WO | 2020006077 | 1/2020 |
| WO | 2020037171 | 2/2020 |
| WO | 2021198045 | 10/2021 |
| WO | 2022026623 | 2/2022 |

OTHER PUBLICATIONS

Lucyszyn, Stepan and Suneat Pranonsatit. "RF MEMS for antenna applications." 2013 7th European Conference on Antennas and Propagation (EuCAP). IEEE, 2013 (Year: 2013) pp. 1988-1992.

Ruiz, Raul et al. "A flexible dipole antenna for direct transduction of microwave radiated power into DC mechanical deflection." Sensors and Actuators: A Physical 340 (2022): 113536 (Year: 2022) 7 pages.

\* cited by examiner

Fig. 5A
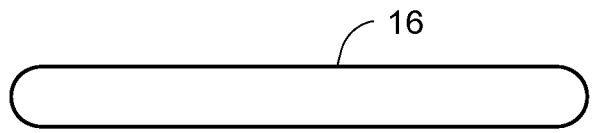
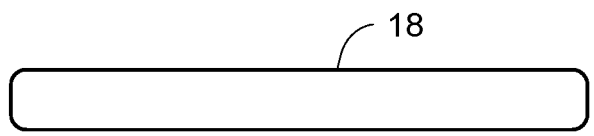
Fig. 5B
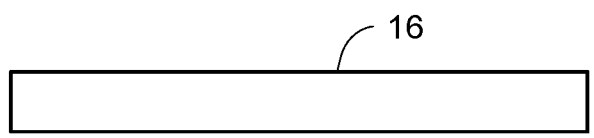
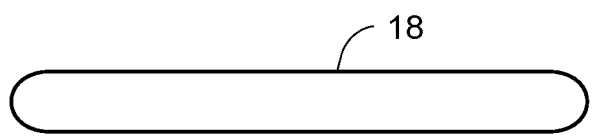
Fig. 5C
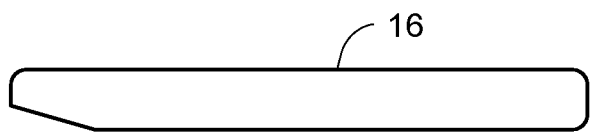
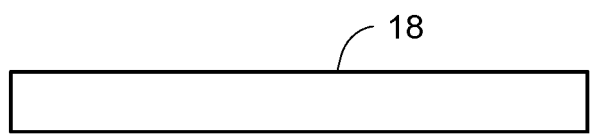

ANALYTE SENSORS WITH POSITION ADJUSTABLE TRANSMIT AND/OR RECEIVE COMPONENTS

FIELD

This disclosure relates generally to apparatus, systems and methods of detecting an analyte via spectroscopic techniques using an analyte sensor that operates in the radio or microwave frequency range of the electromagnetic spectrum.

BACKGROUND

There is interest in being able to detect and/or measure an analyte within a target. Sensors that use radio or microwave frequency bands of the electromagnetic spectrum for collection of analyte data are disclosed in WO 2019/217461, U.S. Pat. Nos. 11,063,373, 11,058,331, 11,033,208, 11,284,819 11,284,820, 10,548,503, 11,234,619, 11,031,970, 11,223,383, 11,058,317, 11,193,923, 11,234,618, 11,389,091, U.S. 2021/0259571, U.S. 2022/0077918, U.S. 2022/0071527, U.S. 2022/0074870, U.S. 2022/0151553, each of which is incorporated herein by reference in its entirety.

SUMMARY

An analyte sensor described herein detects an analyte via spectroscopic techniques using frequencies in the radio or microwave frequency range of the electromagnetic spectrum. The analyte sensor is configured to permit adjustment of the position(s) of one or more transmit components and/or the position(s) of one or more receive components. Adjusting position (or the like) as used in the description and claims includes changing an angle of the transmit component(s) and/or the receive component(s), and/or moving the transmit component(s) and/or the receive component(s) in one or more X, Y, Z directions, and/or changing a shape of the transmit component(s) and/or the receive component(s), and any combinations thereof.

The position adjustment described herein may be referred to as tuning the analyte sensor, and the analyte sensor may be referred to as a tunable analyte sensor. In one embodiment, one or more analyte readings can be performed with the component(s) at one detecting position, one or more analyte readings can be performed with the component(s) at a second detecting position, one or more analyte readings can be performed with the component(s) at a third detecting position, etc.

A non-invasive analyte sensor is configured to detect at least one analyte in a target by transmitting a transmit signal that is in a radio or microwave frequency range of the electromagnetic spectrum into the target containing the at least one analyte, and is configured to detect a response signal that results from transmission of the transmit signal into the target. The at least one component associated with transmitting the transmit signal and/or associated with detecting the response signal is position adjustable relative to a wall of a housing of the non-invasive analyte sensor whereby a position of the at least one component is adjustable. The position adjustment can comprise one or more of: a change in angle; movement toward and away from the target; movement laterally relative to the target; and/or a change in shape.

In another embodiment, a non-invasive analyte sensor is configured to detect at least one analyte in a target by transmitting, from a transmit antenna, a transmit signal that is in a radio or microwave frequency range of the electromagnetic spectrum into the target containing the at least one analyte, and configured to detect, using a receive antenna, a response signal that results from transmission of the transmit signal into the target. At least one component associated with transmitting the transmit signal and/or associated with detecting the response signal is adjustable between a first detecting position at which detection of the at least one analyte takes place and a second detecting position at which detection of the at least one analyte takes place.

In another embodiment, an analyte sensor described herein can comprise at least one transmit antenna that is configured to transmit a transmit signal into a target containing an analyte, and the transmit signal is in a radio or microwave frequency range of the electromagnetic spectrum. The analyte sensor also includes at least one receive antenna that is configured to detect a response that results from transmission of the transmit signal into the target. In addition, at least one transmit component of the analyte sensor and/or at least one receive component of the analyte sensor is position adjustable whereby a position of the at least one transmit component and/or a position of the at least one receive component is adjustable. The position adjustable transmit component and the position adjustable receive component can be the at least one transmit antenna and/or the at least one receive antenna, a transmit signal reflector and/or a receive signal reflector, and any combinations thereof.

Another embodiment of an analyte sensor can comprise a housing including a base wall, a transmit system and a receive system. The analyte sensor is configured to transmit a transmit signal, using at least transmit antenna, into a target containing an analyte. The transmit signal is in a radio or microwave frequency range of the electromagnetic spectrum. The analyte sensor is also configured to detect a response, using at least one receive antenna, resulting from transmission of the transmit signal into the target. At least one transmit component and/or at least one receive component is position adjustable whereby a position of the at least one transmit component and/or a position of the at least one receive component is adjustable relative to the base wall of the housing. The position adjustable transmit component and the position adjustable receive component can be the at least one transmit antenna and/or the at least one receive antenna, a transmit signal reflector and/or a receive signal reflector, and any combinations thereof.

In another embodiment, a method of detection of an analyte using an analyte sensor comprises adjusting, from a first detecting position to a second detecting position, at least one transmit component of the analyte sensor and/or at least one receive component of the analyte sensor. With the at least one transmit component and/or the at least one receive component at the second detecting position, a transmit signal is transmitted into a target containing the analyte using at least one transmit antenna of the analyte sensor, where the transmit signal is in a radio or microwave frequency range of the electromagnetic spectrum, and a response is detected, using at least one receive antenna of the analyte sensor, that results from transmission of the transmit signal into the target.

In another embodiment, a method of detection of an analyte in a target using an analyte sensor comprises: with at least one transmit component of the analyte sensor and/or at least one receive component of the analyte sensor at a first detecting position, transmitting a first transmit signal that is in a radio or microwave frequency range of the electromagnetic spectrum into the target containing the analyte using at least one transmit antenna and detecting a first response, using at least one receive antenna of the analyte sensor, that results from transmission of the first transmit signal into the target. Thereafter, the at least one transmit component and/or the at least one receive component is adjusted from the first detecting position to a second detecting position. With the at least one transmit component and/or the at least one receive component at the second detecting position, a second transmit signal that is in a radio or microwave frequency range of the electromagnetic spectrum is transmitted into the target using the at least one transmit antenna and a second response is detected, using the at least one receive antenna, that results from transmission of the second transmit signal into the target.

The analyte sensor described herein can include two or more antennas. In an embodiment, one of the antennas can be the transmit antenna while one of the antennas can be the receive antenna. In another embodiment, any one or more of the antennas can be selected to operate as the transmit antenna(s) and any one or more of the antennas can be selected to operate as the receive antenna(s).

DRAWINGS

FIGS. 5A-5C depict possible examples of the transmit and receive antennas that can be used in the analyte sensors described herein.

DETAILED DESCRIPTION

Figure 1:
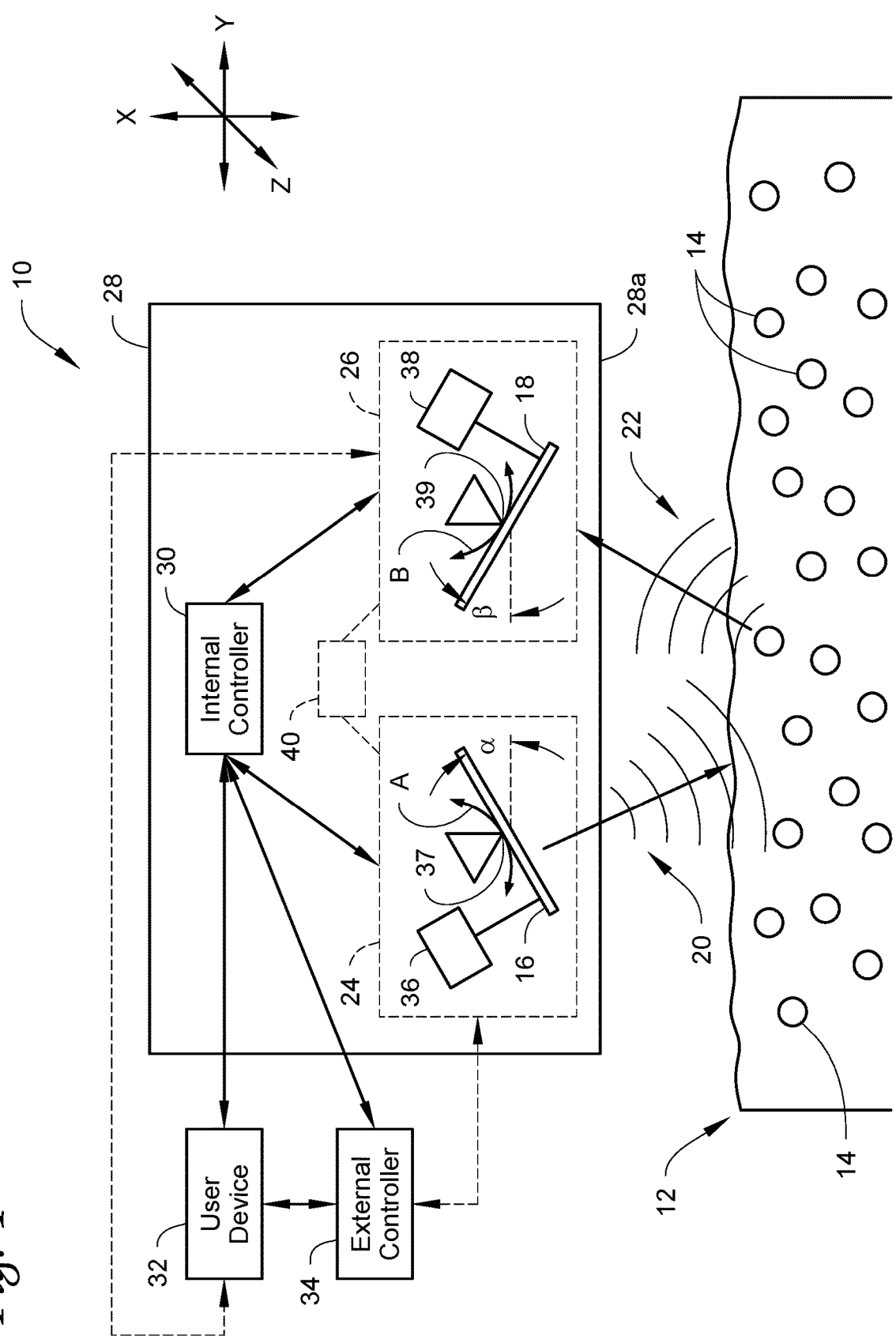
FIG. 1 depicts one embodiment of an analyte sensor described herein.

The following is a detailed description of apparatus, systems and methods of detecting an analyte via spectroscopic techniques using frequencies in the radio or microwave frequency bands of the electromagnetic spectrum. An analyte sensor described herein includes at least one antenna which functions as a transmit antenna to transmit an electromagnetic signal in the radio or microwave frequency range into a target and at least one antenna which functions as a receive antenna that receives an electromagnetic signal in the radio or microwave frequency range resulting from transmission of the electromagnetic signal into the target. The analyte sensor described herein operates by transmitting an electromagnetic signal in the radio or microwave frequency range of the electromagnetic spectrum toward and into a target using the at least one transmit antenna. A returning signal that results from the transmission of the transmitted signal is detected by the at least one receive antenna. The signal(s) detected by the receive antenna(s) can be analyzed to detect the analyte based on the intensity of the received signal(s) and reductions in intensity at one or more frequencies where the analyte absorbs the transmitted signal.

The analyte sensor described herein can be described as being non-invasive meaning that the sensor remains outside the target, such as the human body, and the detection of the analyte occurs without requiring removal of fluid or other removal from the target, such as the human body, although the non-invasive analyte sensor may be used to detect one or more analytes in fluid or other material that has been removed from the target. In the case of sensing an analyte in the human body, this non-invasive sensing may also be referred to as in vivo sensing.

The analyte sensor is configured to transmit generated transmit signals that are in a radio or microwave frequency range of the electromagnetic spectrum from the transmit antenna(s) into a target containing an analyte, and to also detect responses that result from transmission of the transmit signals into the target. Examples of detecting analytes using non-invasive spectroscopy sensors operating in the radio or microwave frequency range of the electromagnetic spectrum are described in WO 2019/217461, U.S. Pat. Nos. 11,063, 373, 11,058,331, 11,033,208, 11,284,819, 11,284,820, 10,548,503, 11,234,619, 11,031,970, 11,223,383, 11,058, 317, 11,193,923, 11,234,618, 11,389,091, U.S. 2021/ 0259571, U.S. 2022/0077918, U.S. 2022/0071527, U.S. 2022/0074870, U.S. 2022/0151553, the entire contents of each are incorporated herein by reference.

In one embodiment, the analyte sensor described herein can be used to detect the presence of at least one analyte in a target. In another embodiment, the analyte sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, one or more of blood, interstitial fluid, cerebral spinal fluid, lymph fluid or urine, human tissue, animal tissue, plant tissue, an inanimate object, soil, genetic material, or a microbe.

The analyte(s) can be any analyte that one may wish to detect. The analyte can be human or non-human, animal or non-animal, biological or non-biological. For example, the analyte(s) can include, but is not limited to, one or more of glucose, blood alcohol, oxygen, white blood cells, or luteinizing hormone. The analyte(s) can include, but is not limited to, a chemical, a combination of chemicals, a virus, a bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. In an embodiment, the analyte may be simultaneously detected from both blood and interstitial fluid. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, particular conformations or conjugations of hemoglobin such as oxy-hemoglobin, deoxyhemoglobin, carboxyhemoglobin, and the like, hepatitis B virus, HCMV, HIV-1, HTLV-1, Leber hereditary optic neuropathy, MCAD, RNA, PKU, Plasmodium vivax, sexual differentiation, 21-deoxycortisol); des-butylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1,β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; zinc protoporphyrin; prostaglandins such as PGF2α and PGE2; hormones such as estrogen, progesterone, and/or follicle stimulating hormone (FSH).

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Referring now to FIG. 1, an embodiment of a non-invasive analyte sensor system with an analyte sensor 10 is illustrated. The analyte sensor 10 is depicted relative to a target 12 that contains an analyte of interest 14, for example an analyte in blood and/or in interstitial fluid in a human body. In this example, the sensor 10 is depicted as including a transmit antenna/element 16 (hereinafter "transmit antenna 16") and a receive antenna/element 18 (hereinafter "receive antenna 18"). The transmit antenna 16 is positioned, arranged and configured to transmit a transmit signal 20 that is the radio frequency (RF) or microwave range of the electromagnetic spectrum into the target 12. The transmit signal 20 can have a frequency that is in the range from about 10 kHz to about 100 GHz. In another embodiment, the frequency can be in a range from about 300 MHz to about 6000 MHz. In an embodiment, a number of discrete transmit signals can be transmitted in a frequency sweep through a range of frequencies that are within the range of about 10 kHz to about 100 GHz, or in another embodiment a range of about 300 MHz to about 6000 MHz. An example of conducting frequency sweeps in an analyte sensor is disclosed in U.S. Pat. No. 11,033,208 the entire contents of which are incorporated herein by reference.

The receive antenna 18 is positioned, arranged, and configured to detect one or more electromagnetic response signals 22 that result from the transmission of the transmit signal 20 by the transmit antenna 16 into the target 12 and impinging on the analyte 14. In an embodiment, the receive antenna 18 can detect an electromagnetic signal having a frequency that is in the range from about 10 kHz to about 100 GHz, or in another embodiment a range from about 300 MHz to about 6000 MHz.

The transmit antenna 16 and the receive antenna 18 can each comprise a longitudinal strip of conductive material such as metal or other material that can transmit and/or receive signals in the radio or microwave frequency range of the electromagnetic spectrum. In an embodiment, the antennas 16, 18 can have geometries that differ from each other. For example, FIGS. 5A-5C illustrate possible non-limiting examples of the shapes of the antennas 16, 18. Referring to FIG. 5A, the antenna 16 is depicted as having a stadium shape (a stadium shape is a two-dimensional geometric shape constructed of a rectangle with semicircles at opposite ends) and the antenna 18 is depicted as having a rounded rectangle shape (a rounded rectangle shape is a two-dimensional geometric shape constructed of a rectangle with radiuses at each corner of the rectangle). Referring to FIG. 5B, the antenna 16 is depicted as having a rectangular shape while the antenna 18 is depicted as having a stadium shape. Referring to FIG. 5C, the antenna 16 is depicted as having a modified rounded rectangle shape with one end tapered while the antenna 18 is depicted as having a rectangular shape. Many other shapes and combinations of shapes are possible. The different shapes of the antennas help to decouple the antennas 16, 18 from one another to minimize direct receipt of the signal transmitted by the transmit antenna 16 by the receive antenna 18, and increases the portion of the signal(s) detected by the receive antenna 18 that is the response signal(s) 22 from the target 12. Further information on antenna shapes to decouple transmit and receive antennas from one another in an analyte sensor is disclosed in U.S. Pat. No. 11,033,208 the entire contents of which are incorporated herein by reference.

In another embodiment, the transmit antenna 16 and the receive antenna 18 can have the same shape as one another. For example, the transmit antenna 16 and the receive antenna 18 can each have a rectangular shape, a stadium shape, a rounded rectangle shape, or other shapes in common with each other.

Returning to FIG. 1, the transmit antenna 16 may be considered part of a transmit system 24 which is depicted in broken lines and which may include other components in addition to the transmit antenna 16. Similarly, the receive antenna 18 may be considered part of a receive system 26 which is depicted in broken lines and which may include other components in addition to the receive antenna 18. The transmit system 24 and the receive system 26 are depicted as being disposed (partially or entirely) within a housing 28. An internal controller 30, which is disposed in the housing 28, is connected to and controls operation of the transmit system 24 and the receive system 26. For example, the controller 30 can include a transmit circuit that is connectable to the transmit antenna 16 and that generates the transmit signal(s) 20 to be transmitted by the transmit antenna 16, and a receive circuit that is connectable to the receive antenna 18 to convert the electromagnetic energy detected by the receive antenna 18 into one or more signals reflective of the response signal(s) 22. Alternatively, the transmit circuit may be part of the transmit system 24 and the receive circuit may be part of the receive system 26. The controller 30 may be part of the transmit system 24, part of the receive system 26, or the transmit system 24 may include a controller that is separate from a controller included in the receive system 26. The sensor 10 can also include a power supply, such as a battery (not shown). In some embodiments, power can be provided from mains power, for example by plugging the sensor 10 into a wall socket via a cord connected to the sensor 10, or by another external power source. Further information on a transmit circuit and a receive circuit in an analyte sensor is disclosed in U.S. Pat. No. 11,063,373 the entire contents of which are incorporated herein by reference.

The sensor 10 can be in communication with a user device 32, such as a mobile phone, tablet, lap top computer, or the like. The user device 32 can be connected to the sensor 10 wirelessly or via a wire. Data from the sensor 10 can be transmitted to the user device 32 and/or the user device 32 can control operation of the sensor 10. The user device 32 may also be in communication with an external controller 34 which may receive sensor data from the user device 32 and/or generate control commands that are sent to the sensor 10 via the user device 32. Alternatively, the external controller 34 may be in direct communication with the internal controller 30, or the external controller 34 may be in direct communication with and control components of the sensor 10, such as the transmit system 24 and/or the receive system 26.

One or more components of the transmit system 24 and/or one or more components of the receive system 26 are adjustably mounted to permit adjustment of the position(s) of one or more transmit components of the transmit system 24 and/or adjustment of the position(s) of one or more receive components of the receive system 26. Adjusting the position (or the like) includes changing an angle of the transmit component(s) and/or the receive component(s), and/or moving the transmit component(s) and/or the receive component(s) in one or more X, Y, Z directions, and/or changing a shape of the transmit component(s) and/or the receive component, and any combinations thereof. As used herein, adjusting the position is intended to encompass any intentional, controlled movement of one or more components of the sensor 10 from one detecting position to another detecting position that results in a change in the sensing performance of the sensor 10. A change in performance can include, but is not limited to, changing an angle at which the transmit signal is transmitted into the target by the sensor 10, changing the angle at which the response signal is received by the sensor 10, moving a component closer to or further away from the target 12, changing the relative positioning between the one or more components and the target 12, changing the relative positioning between one or more components of the transmit system 24 and one or more components of the receive system 26, and the like.

One embodiment of adjusting position depicted in FIG. 1 is changing the angle of the transmit antenna 16 and/or changing the angle of the receive antenna 18. In this embodiment, one or both of the transmit antenna 16 and the receive antenna 18 are adjustably mounted so as to permit adjustment of the angle of the antenna 16, 18. For example, the transmit antenna 16 is depicted as being mounted in a manner to permit the antenna 16 to be tilted in the direction of the arrows A to change the angle α thereof. The adjustable mounting can be achieved in any manner that permits adjustment of the angle of the antenna 16, for example by mounting the antenna 16 via a universal joint 37 that permits universal tilting of the antenna 16 in a two-dimensional plane (such as, but not limited to, an X-Y plane), or three-dimensional tilting. An actuator 36 can be connected to the antenna 16 to achieve the tilting. Tilting of the antenna 16 can be used to change the angle at which the transmit signal 20 is transmitted into the target 12 and thus changes the angle at which the transmit signal 20 impinges on the analyte 14. The actuator 36 can be any actuator that is suitable to tilt the antenna 16 including, but not limited to, a micro-electromechanical (MEMS) motor, any electromechanical actuator such as a MEMS magnetic actuator, a magnetic actuator, an electric actuator, a thermal actuator, a super-coiled polymer actuator, a piezoelectric actuator, an electrostatic actuator, an electro-optical actuator, an optical actuator, a photostrictive actuator, and others.

In an embodiment, the angle α may range from ±90 degrees relative to the horizontal axis (depicted in broken lines) in an X-Y plane shown in FIG. 1. In another embodiment, the angle α may range from ±75 degrees relative to the horizontal axis. In still another embodiment, the angle a may range from ±60 degrees relative to the horizontal axis. In still another embodiment, the angle a may range from ±45 degrees relative to the horizontal axis. In still another embodiment, the angle a may range from ±30 degrees relative to the horizontal axis. However, other angles and ranges of angles are possible. In another embodiment, the range of angles can be centered about (or referenced relative to) an axis other than the horizontal axis, for example the vertical axis of the X-Y plane shown in FIG. 1, a diagonal axis extending in a direction that is angled with respect to the vertical and horizontal axes, or the like.

Similarly, the receive antenna 18 is depicted as being mounted in a manner to permit the antenna 18 to be tilted in the direction of the arrows B to change the angle β thereof. The adjustable mounting can be achieved in any manner that permits adjustment of the angle of the antenna 16, for example by mounting a universal joint 39 that permits universal tilting of the antenna 18 in a two-dimensional plane (such as, but not limited to, an X-Y plane), or three-dimensional tilting. An actuator 38 can be connected to the antenna 18 to achieve the tilting. Tilting of the antenna 18 can be used to change the angle at which the receive antenna 18 receives the response signal 22. The actuator 38 can be any actuator that is suitable to tilt the antenna 18 including, but not limited to, a micro-electromechanical (MEMS) motor, any electromechanical actuator such as a MEMS magnetic actuator, a magnetic actuator, an electric actuator, a thermal actuator, a super-coiled polymer actuator, a piezoelectric actuator, an electrostatic actuator, an electro-optical actuator, an optical actuator, a photostrictive actuator, and others.

In an embodiment, the angle α may range from ±90 degrees relative to the horizontal axis (depicted in broken lines) in an X-Y plane shown in FIG. 1. In another embodiment, angle β may range from ±75 degrees relative to the horizontal axis. In still another embodiment, the angle β may range from ±60 degrees relative to the horizontal axis. In still another embodiment, the angle β may range from ±45 degrees relative to the horizontal axis. In still another embodiment, the angle β may range from ±30 degrees relative to the horizontal axis. However, other angles and ranges of angles are possible. In another embodiment, the range of angles can be centered about (or referenced relative to) an axis other than the horizontal axis, for example the vertical axis of the X-Y plane shown in FIG. 1, a diagonal axis extending in a direction that is angled with respect to the vertical and horizontal axes, or the like.

Although both the transmit antenna 16 and the receive antenna 18 are depicted as being tiltable, only the transmit antenna 16 may be tiltable while the receive antenna 18 is fixed, or only the receive antenna 18 may be tiltable while the transmit antenna 16 is fixed.

In this embodiment, a first analyte reading can be performed with one or both of the antennas 16, 18 at a first angle (i.e. to a first detecting position), and after changing the angle of one or more of the antennas 16, 18 to a second angle (i.e. to a second detecting position), a second analyte reading can be performed.

Another embodiment of adjusting position depicted in FIG. 1 is changing the physical position of the transmit antenna 16 and/or the receive antenna 18. In this embodiment, one or both of the transmit antenna 16 and the receive antenna 18 are adjustably mounted so as to permit changes in the physical position thereof in the X, Y, and/or Z axis directions relative to the target 12 and relative to the housing 28. For example, FIG. 1 depicts an actuator 40 connected to the transmit system 24 and to the receive system 26. The actuator 40 can adjust the transmit system 24, and therefore the transmit antenna 16, in the X direction to move the transmit system 24 (and the antenna 16) toward or away from the target 12 or toward or away from a base wall 28a of the housing 28, adjust the transmit system 24 (and therefore the antenna 16) in the Y direction to move the transmit system 24 and the antenna 16 laterally (or side-to-side or left to right when viewing FIG. 1) relative to the target 12 or laterally relative to the base wall 28a of the housing 28, adjust the transmit system 24 and the antenna 16 in the Z direction to move transmit system 24 and the antenna 16 laterally (or forward and backward or into or out of the page when viewing FIG. 1) relative to the target 12 or laterally relative to the base wall 28a of the housing 28, or combinations of X, Y, Z movements. Similarly, the actuator 40 (or a different actuator connected to the receive system 26) can adjust the receive system 26 and the receive antenna 18 in the X direction to move the receive system 26 and the antenna 18 toward or away from the target 12 or toward or away from a base wall 28a of the housing 28, adjust the receive system 26 and the antenna 18 in the Y direction to move receive system 26 and the antenna 18 laterally (or side-to-side or left to right when viewing FIG. 1) relative to the target 12 or laterally relative to the base wall 28a of the housing 28, adjust the receive system 26 and the antenna 18 in the Z direction to move receive system 26 and the antenna 18 laterally (or forward and backward or into or out of the page when viewing FIG. 1) relative to the target 12 or laterally relative to the base wall 28a of the housing 28, or combinations of X, Y, Z movements.

The actuator 40 can be any actuator including, but not limited to, a micro-electromechanical (MEMS) motor, any electromechanical actuator such as a MEMS magnetic actuator, a magnetic actuator, an electric actuator, a thermal actuator, a super-coiled polymer actuator, a piezoelectric actuator, an electrostatic actuator, an electro-optical actuator, an optical actuator, a photostrictive actuator, and others.

Although both the transmit system 24 and the receive system 26 are depicted as being position adjustable, only the transmit system 24 may be position adjustable while the receive system 26 is fixed, or only the receive system 26 may be position adjustable while the transmit system 24 is fixed. In addition, although the actuator 40 is depicted as actuating the transmit system 24 and the receive system 26, separate actuators can be used to actuate the transmit system 24 and the receive system 26.

In this embodiment, a first analyte reading can be performed with one or both of the transmit system 24 and the receive system 24 at a first detecting position, and after changing the physical location of one or both of the transmit system 24 and the receive system 26 to a second detecting position, a second analyte reading can be performed.

Figure 11:
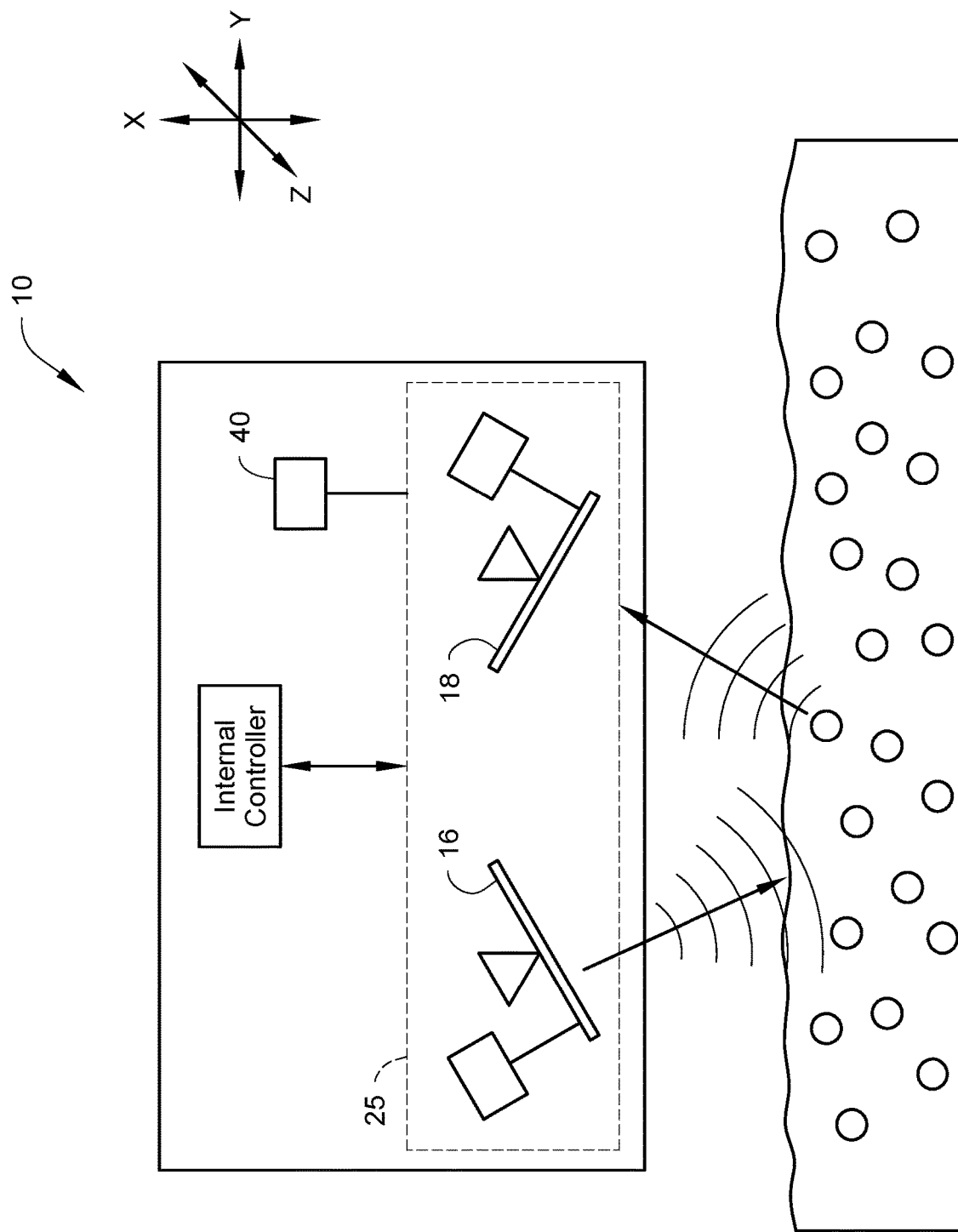
FIG. 11 illustrates still another embodiment of an analyte sensor.

FIG. 11 illustrates another embodiment of the analyte sensor 10. In this embodiment, elements that are similar to or the same as elements in FIG. 1 are referenced using the same reference numerals. In this embodiment, instead of the separate transmit system 24 and the receive system 26 as in FIG. 1, the transmit antenna 16 and the receive antenna 18 are part of a common system 25. The transmit antenna 16 and/or the receive antenna 18 may be mounted in a manner as described above in FIG. 1 to allow the angle of one or both of the transmit antenna 16 and/or the receive antenna 18 to be adjusted. Also, the X, Y, Z position(s) of the system 25, and thus of the transmit antenna 16 and the receive antenna 18, may be adjusted by the actuator 40.

Figure 3:
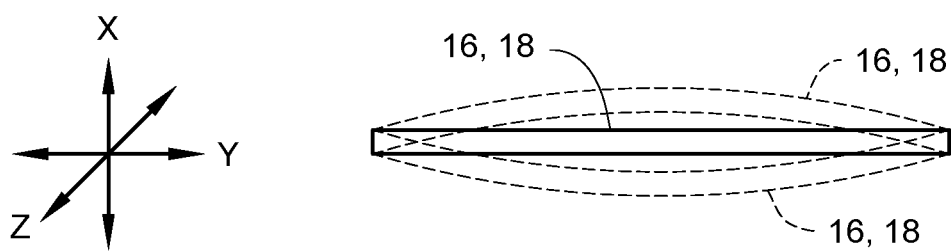
FIG. 3 depicts an example of an antenna of the analyte sensor that can change physical shape.

Referring to FIG. 3, another embodiment of adjusting position includes changing a shape of the transmit component(s) and/or the receive component(s), in particular changing a shape of the transmit antenna 16 and/or changing a shape of the receive antenna 18. For example, FIG. 3 depicts the shape of one or both of the antennas 16, 18 as being modified from a substantially planar shape into a convex shape (upper set of broken lines) or modified into a concave shape (lower set of broken lines). Alternatively, one or both of the antennas 16, 18 can be modified from the planar shape into a twisted shape. Other shape changes are possible. In this embodiment, a first analyte reading can be performed with one or both of the antennas 16, 18 having a first shape (such as the planar shape), and after changing the shape of one or more of the antennas 16, 18, a second analyte reading can be performed.

Referring to FIGS. 1 and 3, the angle of the antennas 16, 18 can be changed by changing an angle of the antennas 16, 18 themselves or changing an angle of substrates on which the antennas 16, 18 are mounted. Similarly, the physical location of the antennas 16, 18 can be changed by changing the physical location of the antennas 16, 18 themselves or changing the locations of substrates on which the antennas 16, 18 are mounted. Similarly, changing the shape of the antennas 16, 18 can be caused by changing the shape of the antennas 16, 18 themselves or changing the shapes of substrates on which the antennas 16, 18 are mounted that results in a change in shape of the antennas 16, 18.

Figure 2:
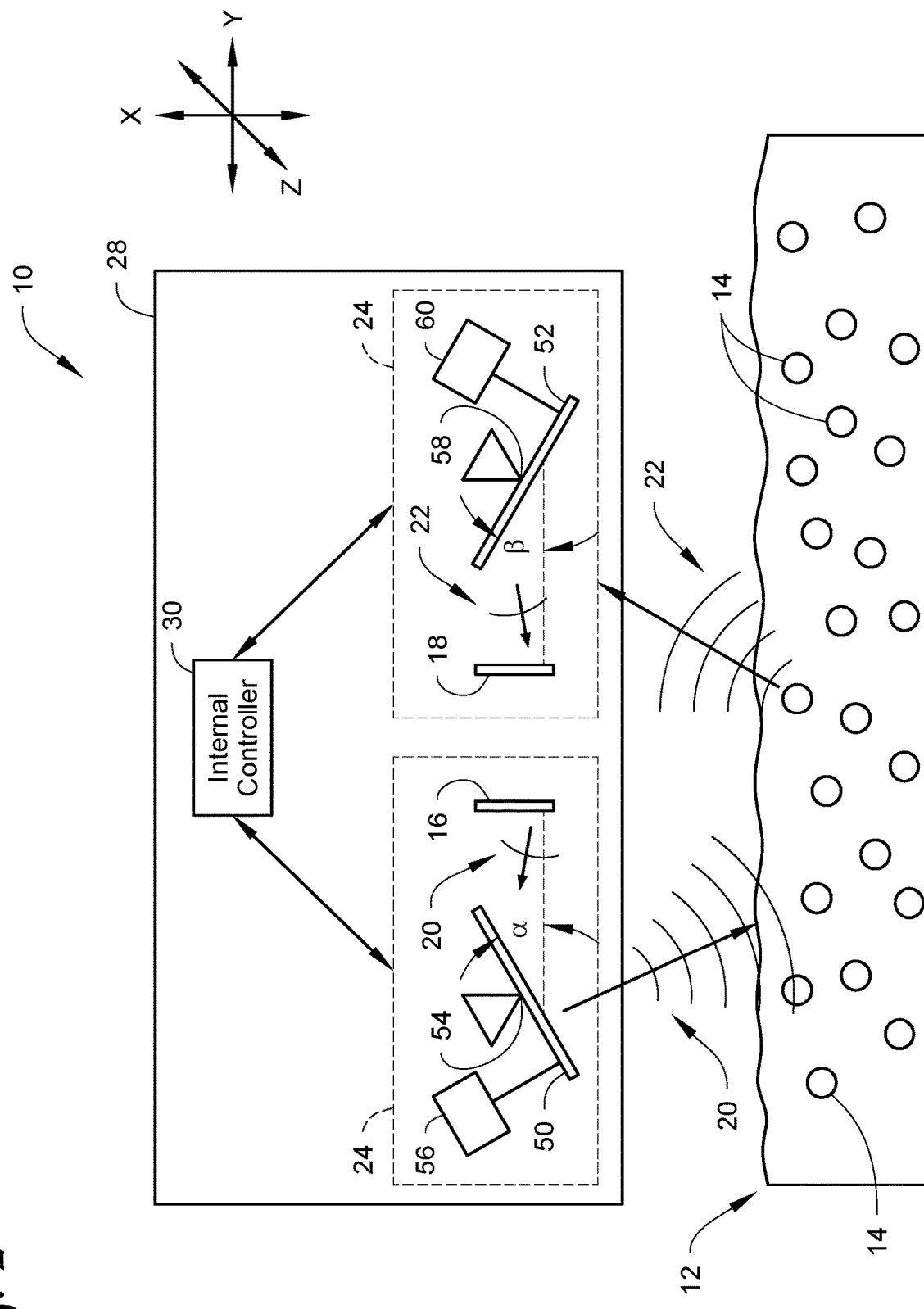
FIG. 2 depicts another embodiment of an analyte sensor described herein.

FIG. 2 depicts another embodiment of the analyte sensor 10. In this embodiment, elements that are similar to or the same as elements in FIG. 1 are referenced using the same reference numerals. In this embodiment, the transmit system 24 is depicted as including a transmit signal reflector 50. The reflector 50 is configured and positioned to reflect the transmit signal 20 that is transmitted by the transmit antenna 16 toward the target 12. The transmit antenna 16 may have a fixed angle, or the angle of the transmit antenna 16 may be adjustable as described in FIG. 1. Similarly, the receive system 26 is depicted as including a receive signal reflector 52. The reflector 52 is configured and positioned to reflect the response signal 22 from the target 12 toward the receive antenna 18. The receive antenna 18 may have a fixed angle, or the angle of the receive antenna 18 may be adjustable as described in FIG. 1. Although the transmit system 24 is depicted as including the signal reflector 50 and the receive system 26 is depicted as including the signal reflector 52, only one of the signal reflectors 50, 52 need be utilized. The signal reflectors 50, 52 can have any construction suitable for reflecting signals in the radio or microwave frequency range. For example, the signal reflectors 50, 52 may be metal plates or any other structure that is suitable for reflecting signals in the radio or microwave frequency range.

In this embodiment, one or both of the signal reflectors 50, 52 are adjustably mounted so as to permit adjustment of the angle of the signal reflectors 50, 52. For example, the signal reflector 50 is depicted as being mounted in a manner to permit the signal reflector 50 to be tilted in a manner similar to the transmit antenna 16 in FIG. 1 to change the angle α thereof. The adjustable mounting can be achieved in any manner that permits adjustment of the angle of the signal reflector 50, for example by mounting the signal reflector 50 via a universal joint 54 that permits universal tilting of the signal reflector 50 in a two-dimensional plane (such as, but not limited to, an X-Y plane), or three-dimensional tilting. An actuator 56 is connected to the signal reflector 50 to achieve the tilting. Tilting of the signal reflector 50 can be used to change the angle at which the transmit signal 20 is transmitted into the target 12 and thus changes the angle at which the transmit signal 20 impinges on the analyte 14. The actuator 56 can be any actuator including, but not limited to, a micro-electromechanical (MEMS) motor, any electromechanical actuator such as a MEMS magnetic actuator, a magnetic actuator, an electric actuator, a thermal actuator, a super-coiled polymer actuator, a piezoelectric actuator, an electrostatic actuator, an electro-optical actuator, an optical actuator, a photostrictive actuator, and others.

In an embodiment, the angle α may range from ±90 degrees relative to a line (depicted in broken line) normal to the plane of the transmit antenna 16. In another embodiment, the angle α may range from ±75 degrees relative to the line normal to the plane of the transmit antenna 16. In still another embodiment, the angle α may range from ±60 degrees relative to the line normal to the plane of the transmit antenna 16. In still another embodiment, the angle α may range from ±45 degrees relative to the line normal to the plane of the transmit antenna 16. In still another embodiment, the angle α may range from ±30 degrees relative to the line normal to the plane of the transmit antenna 16. However, other angles and ranges of angles are possible. In another embodiment, the range of angles can be centered about (or referenced relative to) an axis other than the line normal to the plane of transmit antenna 16, for example the vertical axis or the horizontal axis of the X-Y plane shown in FIG. 2, a diagonal axis extending in a direction angled with respect to the vertical and horizontal axes, or the like.

Similarly, the receive signal reflector 52 is depicted as being mounted in a manner to permit the signal reflector 52 to be tilted in a manner similar to the receive antenna 18 to change the angle β thereof. The adjustable mounting can be achieved in any manner that permits adjustment of the angle of the signal reflector 52, for example by mounting the signal reflector 52 via a universal joint 58 that permits universal tilting of the signal reflector 52 in a two-dimensional plane (such as, but not limited to, an X-Y plane), or three-dimensional tilting. An actuator 60 can be connected to the signal reflector 52 to achieve the tilting. Tilting of the signal reflector 52 can be used to change the angle at which the signal reflector 52 receives the response signal 22. The actuator 60 can be any actuator including, but not limited to, a micro-electromechanical (MEMS) motor, any electromechanical actuator such as a MEMS magnetic actuator, a magnetic actuator, an electric actuator, a thermal actuator, a super-coiled polymer actuator, a piezoelectric actuator, an electrostatic actuator, an electro-optical actuator, an optical actuator, a photostrictive actuator, and others.

In an embodiment, the angle β may range from ±90 degrees relative to a line (depicted in broken lines) normal to the plane of the receive antenna 18. In another embodiment, the angle β may range from ±75 degrees relative to the line normal to the plane of the receive antenna 18. In still another embodiment, the angle β may range from ±60 degrees relative to the line normal to the plane of the receive antenna 18. In still another embodiment, the angle β may range from ±45 degrees relative to the line normal to the plane of the receive antenna 18. In still another embodiment, the angle β may range from ±30 degrees relative to the line normal to the plane of the receive antenna 18. However, other angles and ranges of angles are possible. In another embodiment, the range of angles can be centered about (or referenced relative to) an axis other than the line normal to the plane of receive antenna 18, for example the vertical axis or the horizontal axis of the X-Y plane shown in FIG. 2, a diagonal axis extending in a direction angled with respect to the vertical and horizontal axes, or the like.

Although both the transmit system 24 and the receive system 26 are depicted as including the signal reflectors 50, 52, only a single one of the signal reflectors 50, 52 can be used. For example, the transmit system 24 can include the signal reflector 50 while the receive system 26 does not include the signal reflector 52 in which case the receive antenna 18 directly receives the return signal 22, or the receive system 26 can include the signal reflector 52 while the transmit system 24 does not include the signal reflector 50 in which case the transmit antenna 16 transmits the transmit signal 20 directly into the target 12. In another embodiment, although FIG. 2 depicts the signal reflector 50 and the signal reflector 52 as being tiltable, only the signal reflector 50 may be tiltable while the signal reflector 52 is fixed, or only the signal reflector 52 may be tiltable while the signal reflector 50 is fixed.

In this embodiment, a first analyte reading can be performed with one or both of the signal reflectors 50, 52 at a first angle, and after changing the angle of one or more of the signal reflectors 50, 52 to a second angle, a second analyte reading can be performed.

In addition, the physical position of the transmit system 24 and/or the physical position of the receive system 26 may be adjustable in a manner as described above for FIG. 1, for example by using one or more actuators, including, but not limited to, a micro-electromechanical (MEMS) motor, any electromechanical actuator such as a MEMS magnetic actuator, a magnetic actuator, an electric actuator, a thermal actuator, a super-coiled polymer actuator, a piezoelectric actuator, an electrostatic actuator, an electro-optical actuator, an optical actuator, a photostrictive actuator, and others, connected to the transmit system 24 and/or the receive system 26, whereby the physical positions of the transmit antenna 16 and the transmit signal reflector 50 may be adjusted and/or the physical positions of the receive antenna 18 and the receive signal reflector 52 may be adjusted. Alternatively, the physical positions of the transmit antenna 16 and the transmit signal reflector 50 may be mounted so as to be adjustable relative to one another. For example, the transmit signal reflector 50 may be adjustable in a manner as described above for FIG. 1 while the transmit antenna 16 is fixed, or the transmit antenna 16 may be adjustable in a manner as described above for FIG. 1 while the transmit signal reflector 50 is fixed. Similarly, the physical positions of the receive antenna 18 and the receive signal reflector 52 may be mounted so as to be adjustable relative to one another. For example, the receive signal reflector 52 may be adjustable in a manner as described above for FIG. 1 while the receive antenna 18 is fixed, or the receive antenna 18 may be adjustable in a manner as described above for FIG. 1 while the receive signal reflector 52 is fixed.

In this embodiment, the signal reflector 50 and/or the transmit antenna 16 can be adjustable in the X direction toward or away from the target 12 or toward or away from a base wall 28a of the housing 28; the signal reflector 50 and/or the transmit antenna 16 can be adjustable in the Y direction laterally (or side-to-side or left to right when viewing FIG. 2) relative to the target 12 or laterally relative to the base wall 28a of the housing 28; the signal reflector 50 and/or the transmit antenna 16 can be adjustable in the Z direction laterally (or forward and backward or into or out of the page when viewing FIG. 2) relative to the target 12 or laterally relative to the base wall 28a of the housing 28, or combinations of X, Y, Z movements. Similarly, the signal reflector 52 and/or the receive antenna 18 can be adjustable in the X direction toward or away from the target 12 or toward or away from a base wall 28a of the housing 28; the signal reflector 52 and/or the receive antenna 18 can be adjustable in the Y laterally (or side-to-side or left to right when viewing FIG. 2) relative to the target 12 or laterally relative to the base wall 28a of the housing 28; the signal reflector 52 and/or the antenna 18 can be adjustable in the Z direction laterally (or forward and backward or into or out of the page when viewing FIG. 2) relative to the target 12 or laterally relative to the base wall 28a of the housing 28, or combinations of X, Y, Z movements.

Figure 4:
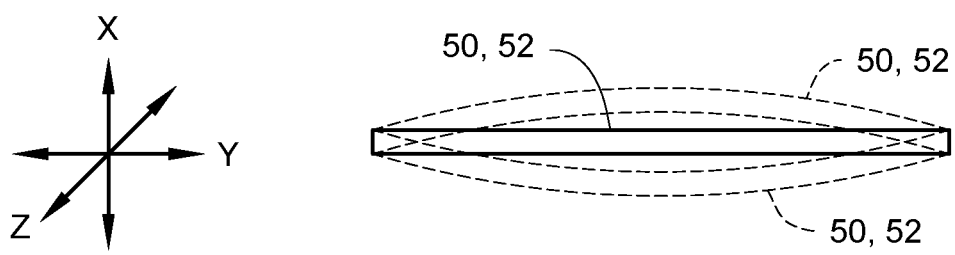
FIG. 4 depicts an example of a signal reflector of the analyte sensor that can change physical shape.

Referring to FIG. 4 along with FIG. 2, another embodiment of adjusting position includes changing a shape of the signal reflector 50 and/or changing a shape of the signal reflector 52. For example, FIG. 4 depicts the shape of one or both of the signal reflector 50, 52 as being modified from a substantially planar shape into a convex shape (upper set of broken lines) or modified into a concave shape (lower set of broken lines). Alternatively, one or both of the signal reflectors 50, 52 can be modified from the planar shape into a twisted shape. Other shapes are possible. In this embodiment, a first analyte reading can be performed with one or both of the signal reflectors 50, 52 having a first shape (such as the planar shape), and after changing the shape of one or more of the signal reflectors 50, 52, a second analyte reading can be performed.

Returning to FIG. 2, in operation, the transmit antenna 16 transmits the transmit signal 20 toward the signal reflector 50 (if used). The signal reflector 50 then reflects the transmit signal 20 toward the target 12. On the receive side, the signal reflector 52 (if used) is positioned to receive the response signal 22 and reflect the response signal 22 toward the receive antenna 18.

Referring to FIGS. 2 and 4, the angle of the signal reflector 50, 52 can be changed by changing an angle of the signal reflectors 50, 52 themselves or changing an angle of substrates on which the signal reflector 50, 52 are mounted. Similarly, the physical location of the signal reflectors 50, 52 can be changed by changing the physical location of the signal reflectors 50, 52 themselves or changing the locations of substrates on which the signal reflector 50, 52 are mounted. Similarly, changing the shape of the signal reflectors 50, 52 can be caused by changing the shape of the signal reflectors 50, 52 themselves or changing the shapes of substrates on which the signal reflectors 50, 52 are mounted that results in a change in shape of the signal reflectors 50, 52.

Figure 10:
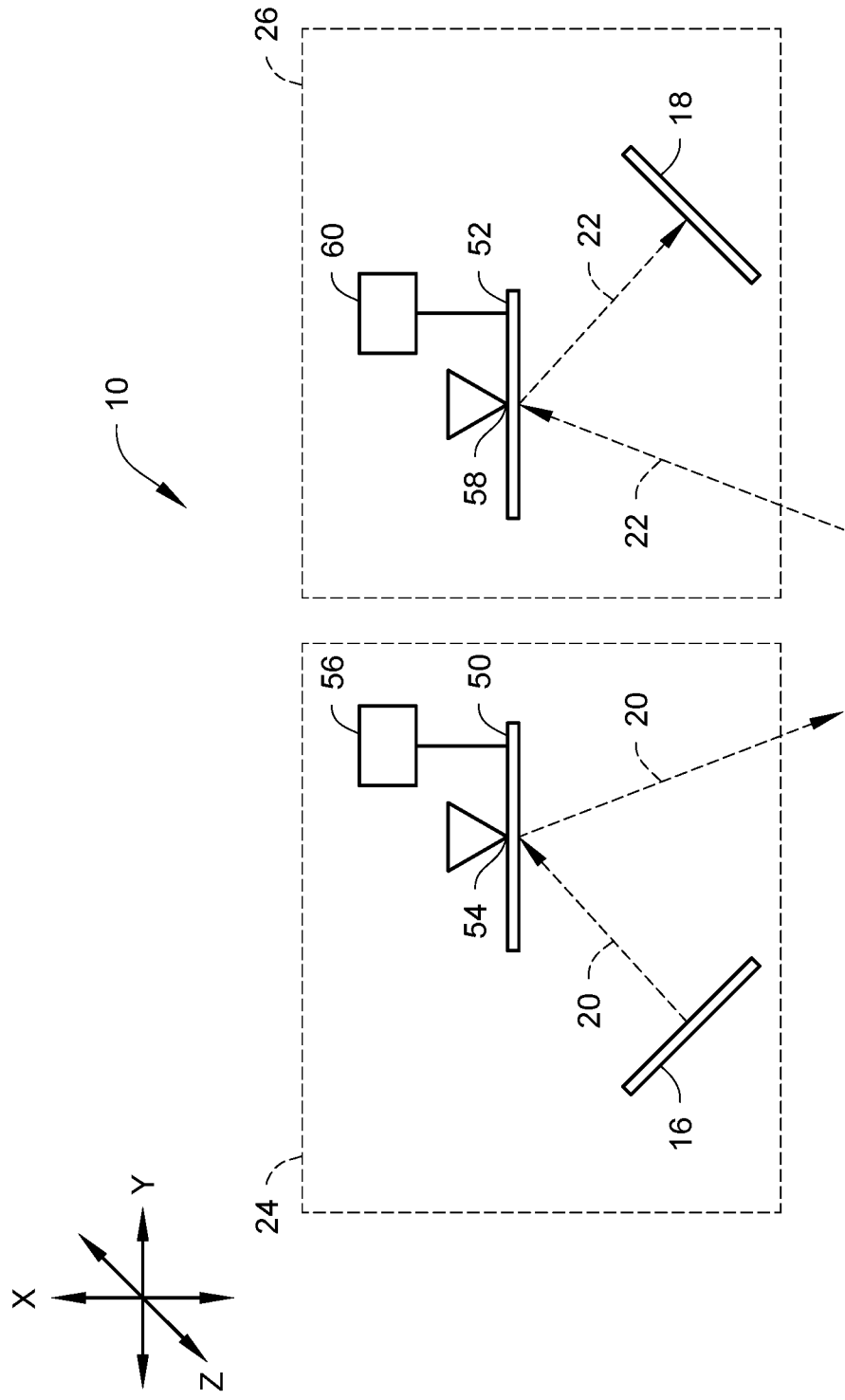
FIG. 10 illustrates another embodiment of an analyte sensor.

FIG. 10 illustrates a part of another embodiment of the analyte sensor 10. In this embodiment, elements that are the same as or similar to elements in FIGS. 1 and 2 are referenced using the same reference numerals. In the embodiment in FIG. 10, the components are the same as in FIG. 2 but are arranged differently. In particular, the antennas 16, 18 are below the reflectors 50, 52. Like in FIG. 2, the angle of the reflectors 50, 52 can be altered using the actuators 56, 60 to suitably reflect the signals 20, 22. In addition, the transmit system 24 and the receive system 26 are adjustable in the X, Y and/or Z axis directions.

Figure 6:
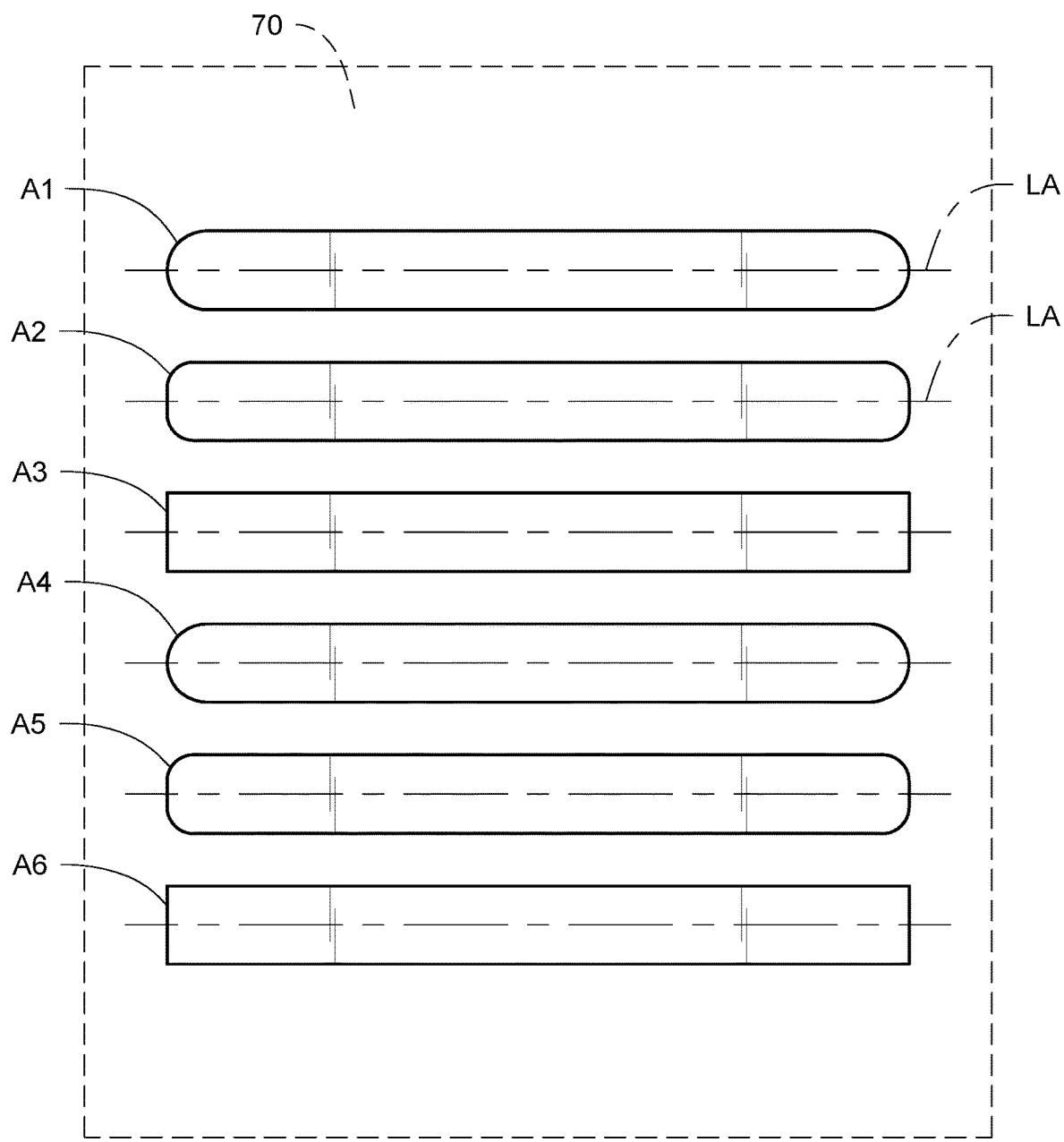
FIG. 6 depicts another example of antennas that can be used in the analyte sensors described herein.

The analyte sensors 10 depicted in FIGS. 1 and 2 are depicted as having two antennas, in particular the transmit antenna 16 and the receive antenna 18. However, other arrangements are possible. For example, the analyte sensors 10 can include an antenna array that has six antennas A1-A6 which may be disposed on a substrate 70 as depicted in FIG. 6. Any one or more of the antennas A1-A6 can be controlled to function as the transmit antenna and any one or more of the antennas A1-A6 can be controlled to function as the receive antenna. U.S. Pat. No. 11,058,331, the entire contents of which are incorporated herein by reference, describes controlling an antenna array with multiple antennas so that any one or more of the antennas can function as a transmit antenna and any one or more of the antennas can function as a receive antenna. In an embodiment, a first antenna array can be included in the analyte sensors 10 to provide antennas that can be controlled to function as the transmit antennas, and a second antenna array can be included in the analyte sensors 10 to provide antennas that can be controlled to function as the receive antennas. In this embodiment, one or both of the first antenna array and the second antenna array can be configured to have an adjustable position or can be incorporated into a transmit system or a receive system including one or more signal reflectors.

Figure 7:
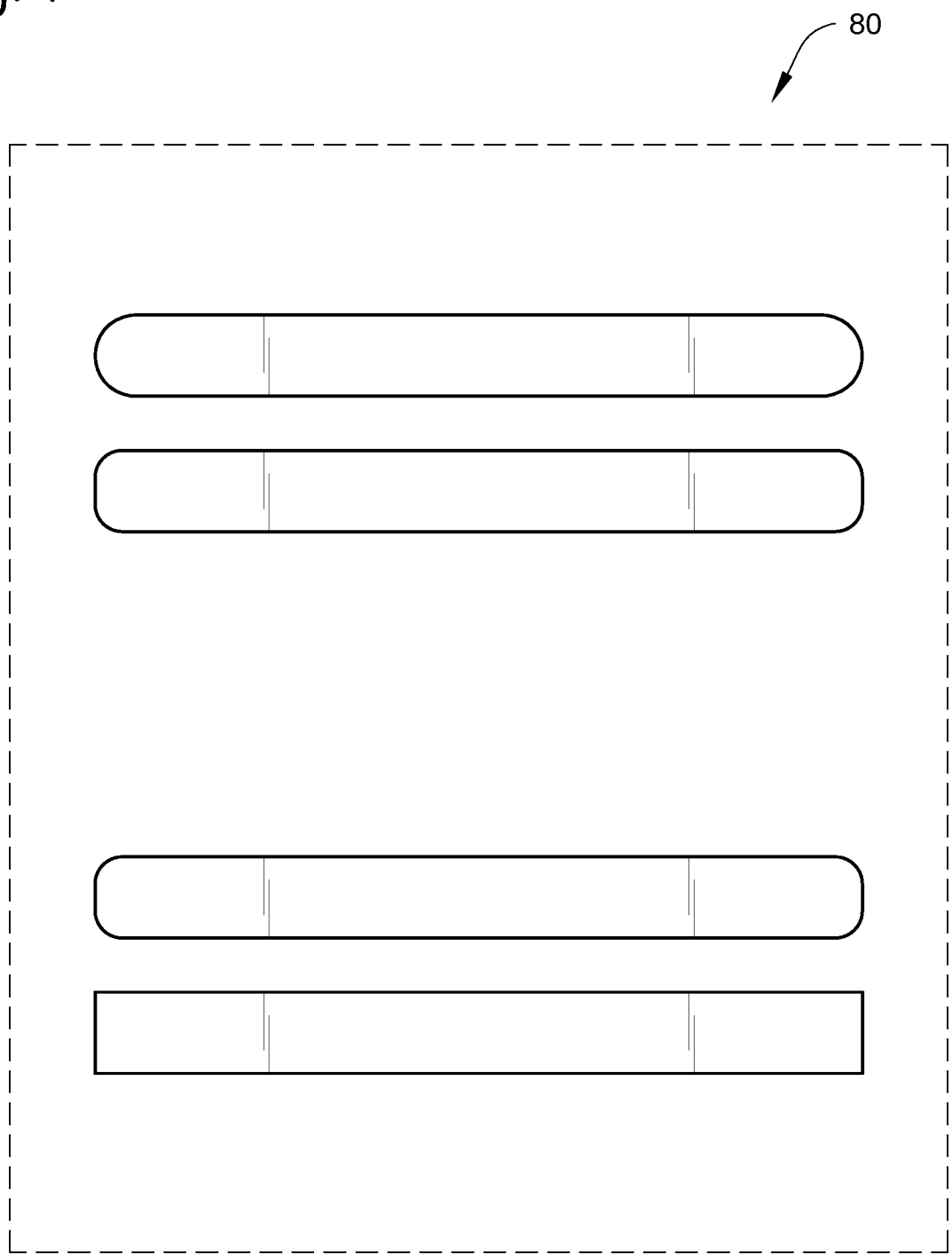
FIG. 7 depicts another example of antennas that can be used in the analyte sensors described herein.
Figure 8:
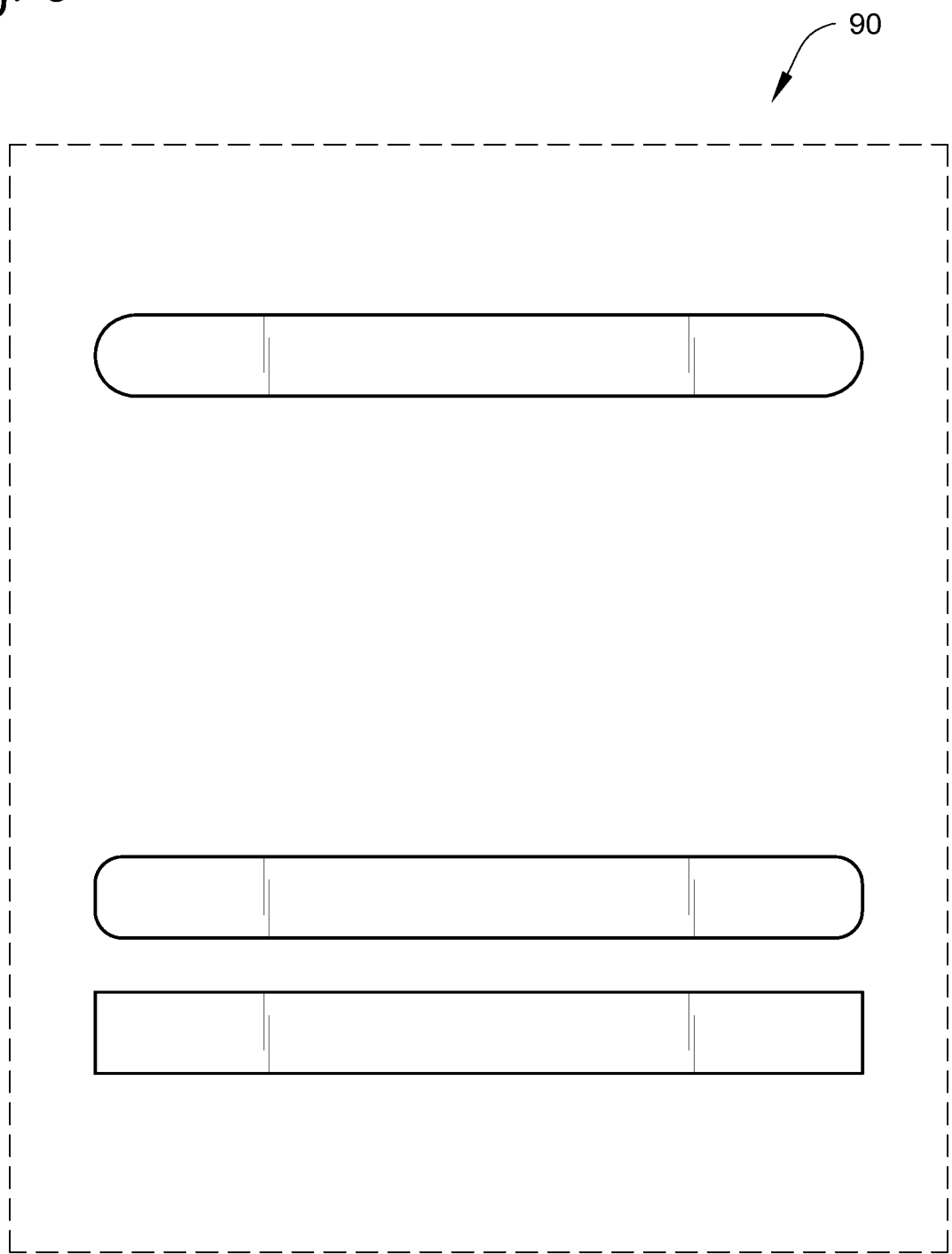
FIG. 8 depicts another example of antennas that can be used in the analyte sensors described herein.

FIG. 7 illustrates an antenna array 80 that can be used in the analyte sensors, where the antenna array 80 has four antennas which may be disposed on a substrate. FIG. 8 illustrates an antenna array 90 that can be used in the analyte sensors, where the antenna array 90 has three antennas which may be disposed on a substrate.

Figure 12:
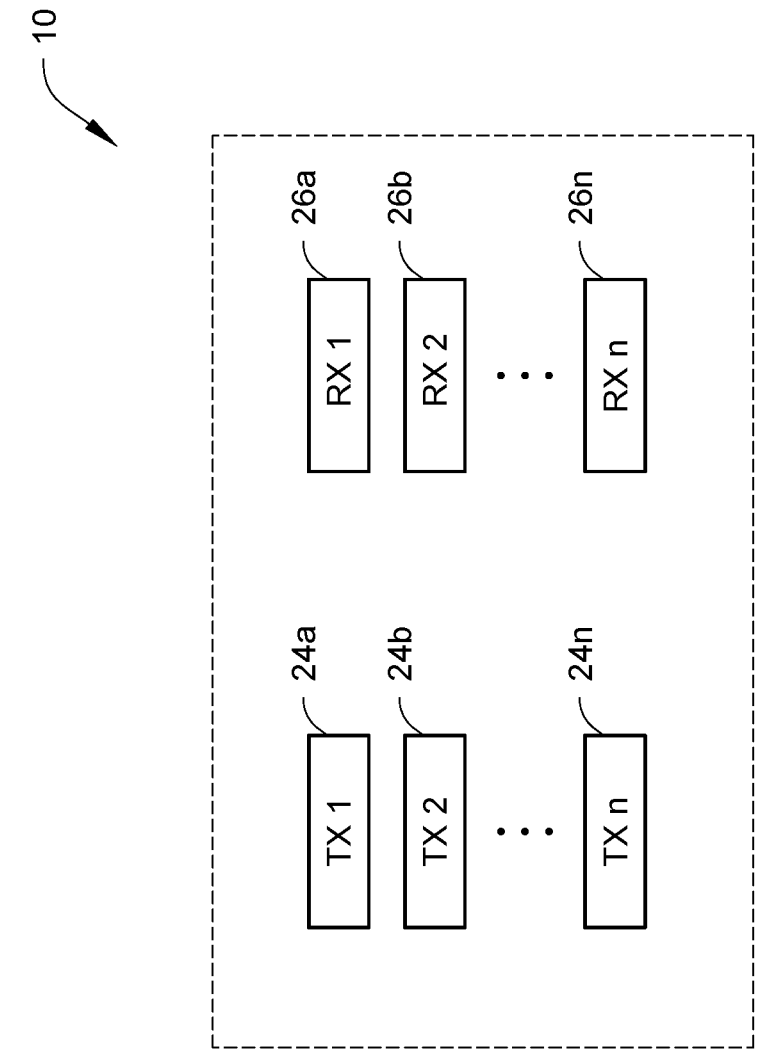
FIG. 12 illustrates still another embodiment of an analyte sensor.

Referring to FIG. 12, another embodiment of the analyte sensor 10 is depicted. In this embodiment, elements that are the same as or similar to elements in FIGS. 1 and 2 are referenced using the same reference numerals. In the embodiment in FIG. 12, the analyte sensor 10 is depicted as including a plurality of the transmit systems 24a, 24b, . . . 24n (the transmit antenna in FIG. 1 or the transmit antenna and the transmit signal reflector in FIG. 2) and/or a plurality of the receive systems 26a, 26b, . . . 26n (the receive antenna in FIG. 1 or the receive antenna and the receive signal reflector in FIG. 2). Similarly, the analyte sensor 10 can include a plurality of the common systems 25 depicted in FIG. 11. The transmit systems 24a, 24b, . . . 24n (if present) may be actuated in X, Y, Z directions collectively or separately using one or more actuators. Similarly, the receive systems 26a, 26b, . . . 26n (if present) may be actuated in X, Y, Z directions collectively or separately using one or more actuators. The transmit systems 24a, 24b, . . . 24n (if present) may be controlled to operate simultaneously, i.e. they simultaneously transmit respective transmit signals, or controlled to operate one after the other (i.e. the transmit system 24a may transmit a first transmit signal, followed by the transmit system 24b transmitting a second transmit signal, etc.). Similarly, the receive systems 26a, 26b, . . . 26n (if present) may be controlled to operate simultaneously, i.e. they simultaneously receive respective response signals, or controlled to operate one after the other (i.e. the receive system 26a may receive a first response signal, followed by the receive system 26b receiving a second response signal, etc.). In addition, the analyte sensor 10 can be controlled so that the receive system 26a receives a response signal that results from the transmit signal that is transmitted by the transmit antenna of the transmit system 24b, . . . 24n. In other words, the receive system 26a does not need to function only with the transmit system 24a, the receive system 26b does not need to function only with the transmit system 24b, etc.

Figure 9:
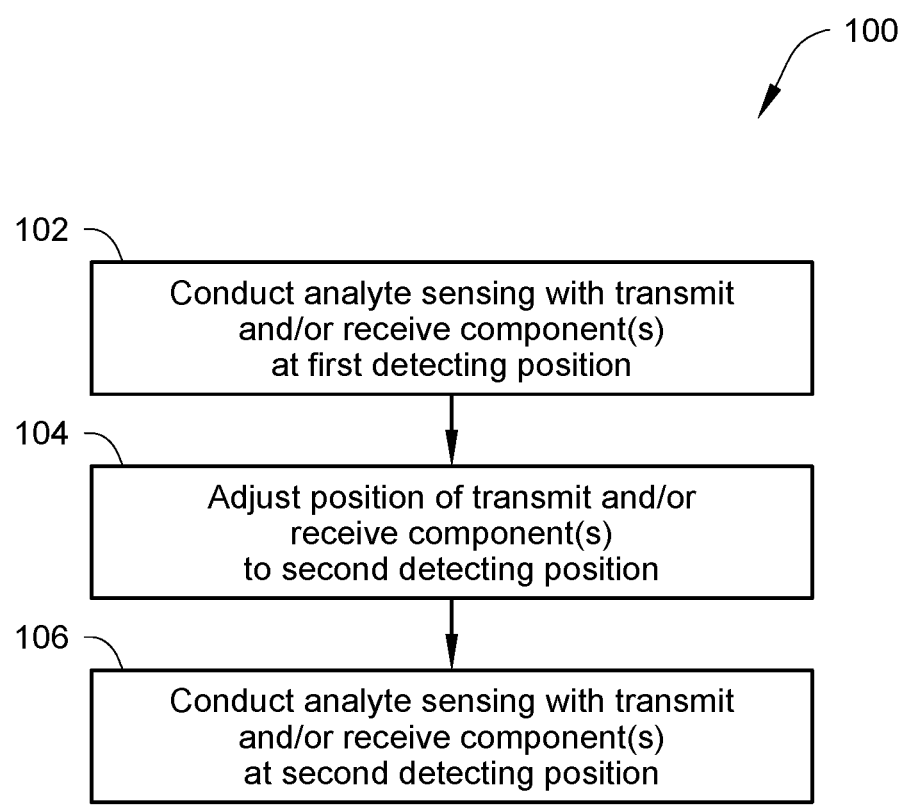
FIG. 9 depicts a method of detection of an analyte using an analyte sensor described herein.

With reference to FIG. 9, a method 100 of operating the analyte sensors 10 described herein is depicted. At box 102, a first analyte sensing is performed with the transmit and/or receive component(s) (for example, the transmit antenna and/or the receive antenna; the transmit signal reflector and/or the receive signal reflector; etc.) at a first detecting position (for example, a first angle, a first X, Y, Z position, a first physical shape, etc.). Thereafter, at box 104, the position of the transmit and/or receive component(s) is adjusted from the first detecting position to a second detecting position. At box 106, a second analyte sensing is performed with the transmit and/or receive component(s) at the second detecting position.

In an embodiment, the analyte sensors 10 may operate based on coordination between the frequency of the transmitted signals and the position of the transmit and/or receive component. For example, a first frequency sweep can be conducted over a range of frequencies and with the transmit and/or receive component at a first position; a second frequency sweep can be conducted over the same range of frequencies and with the transmit and/or receive component at a second position; etc.

For example, assuming a construction similar to FIG. 1 with the angle of the transmit antenna 16 being adjustable, the following frequency sweeps can be performed:

TABLE 1

| Sweep 1 | | Sweep 2 | |
| --- | --- | --- | --- |
| Frequency | Transmit Antenna Position | Frequency | Transmit Antenna Position |
| F1 | α1 | F1 | α2 |
| F2 | α1 | F2 | α2 |
| F3 | α1 | F3 | α2 |
| . | α1 | . | α2 |
| . | α1 | . | α2 |
| . | α1 | . | α2 |
| Fn | α1 | Fn | α2 |

In this embodiment, the transmit antenna is at the same angle α1 over the first frequency sweep, and at the same angle α2 over the second frequency sweep. The receive antenna, the transmit signal reflector and/or the receive signal reflector, can be controlled in the same manner or in a different manner.

In another example, in a frequency sweep, the position of the transmit and/or receive component can be changed in correspondence with each change in frequency. For example, assuming a construction similar to FIG. 1 with the angle of the transmit antenna 16 being adjustable, the following frequency sweep can be performed:

TABLE 2

| Frequency (F) | Transmit Antenna Position (P) |
| --- | --- |
| F1 | P1 |
| F2 | P2 = P1 ± Δ1 |
| F3 | P3 = P2 ± Δ1 |
| . | . |
| . | . |
| . | . |
| Fn | Pn |

In this embodiment, the position, such as the angle, of the transmit antenna 16 is changed (incremented or decremented) with each change in frequency. The receive antenna, the transmit signal reflector and/or the receive signal reflector, can be controlled in the same manner or in a different manner.

The sweeps in Tables 1 and 2 includes a plurality of frequency steps 1, 2 . . . n each of which defines an incremental change (increase or decrease) in frequency from one target frequency to the next target frequency. The frequency steps in the frequency sweep can be the same as one another or some of the frequency steps can be different from one another. For example, in one embodiment, each frequency step can be 1 Hz or 1 kHz or 1 THz, 5 Hz or 5 kHz or 5 THz, 10 Hz or 10 kHz or 10 THz, etc. In addition, in Table 2, the antenna position can change by an incremental amount with each frequency step, or in Table 1 the antenna position can change by an incremental amount from the first frequency sweep to the second frequency sweep.

In a specific example of the example frequency sweep in Table 2, each step from one frequency to the next can be an increase of, for example, 10 Hz. In addition, the angle a of the transmit antenna can be changed (increased or decreased) by a defined increment with each frequency step. For example, the increment of change of the angle a with each frequency step can be, for example, a change of ±0.25 degrees, ±0.5 degrees, ±0.75 degrees, ±1.0 degree, ±5.0 degrees, ±10.0 degrees, ±20.0 degrees or the like, and combinations thereof. Many other frequency sweeps with different frequency steps and changes in angle a are possible.

In another embodiment, the relationship between the frequency and the transmit antenna (or other transmit component or receive component) position can be defined by a function, such as higher-order polynomial functions, for example quadratic, cubic, quartic functions, etc.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A method of detection of an analyte using a non-invasive analyte sensor, comprising:
adjusting, from a first detecting position to a second detecting position, at least one transmit component of the non-invasive analyte sensor and/or at least one receive component of the non-invasive analyte sensor;
with the at least one transmit component and/or the at least one receive component at the second detecting position, transmitting a transmit signal into a target containing the analyte using at least one transmit antenna of the non-invasive analyte sensor, the transmit signal is in a radio or microwave frequency range of the electromagnetic spectrum, and detecting a response, using at least one receive antenna of the non-invasive analyte sensor, that results from transmission of the transmit signal into the target.

2. The method of claim 1, further comprising:
with the at least one transmit component and/or the at least one receive component at the first detecting position, transmitting another transmit signal into the target using the at least one transmit antenna, the another transmit signal is in a radio or microwave frequency range of the electromagnetic spectrum, and detecting a response, using the at least one receive antenna, that results from transmission of the another transmit signal into the target.

3. The method of claim 1, comprising adjusting, from the first detecting position to the second detecting position, the at least one transmit component and the at least one receive component.

4. The method of claim 1, comprising adjusting, from the first detecting position to the second detecting position, the at least one transmit component, and the at least one transmit component comprises the at least one transmit antenna.

5. The method of claim 4, wherein adjusting, from the first detecting position to the second detecting position, the at least one transmit antenna comprises adjusting an angle of the at least one transmit antenna.

6. The method of claim 1, further including at least one transmit signal reflector that reflects the transmit signal transmitted by the at least one transmit antenna; and adjusting, from the first detecting position to the second detecting position, the at least one transmit component, and the at least one transmit component comprises the at least one transmit signal reflector.

7. The method of claim 6, wherein adjusting, from the first detecting position to the second detecting position, the at least one transmit signal reflector comprises adjusting an angle of the at least one transmit signal reflector.

8. The method of claim 1, comprising adjusting, from the first detecting position to the second detecting position, the at least one receive component, and the at least one receive component comprises the at least one receive antenna.

9. The method of claim 8, wherein adjusting, from the first detecting position to the second detecting position, the at least one receive antenna comprises adjusting an angle of the at least one receive antenna.

10. The method of claim 1, further including at least one receive signal reflector that reflects the response toward the at least one receive antenna; and adjusting, from the first detecting position to the second detecting position, the at least one receive component, and the at least one receive component comprises the at least one receive signal reflector.

11. The method of claim 10, wherein adjusting, from the first detecting position to the second detecting position, the at least one receive signal reflector comprises adjusting an angle of the at least one receive signal reflector.

12. The method of claim 1, wherein adjusting, from the first detecting position to the second detecting position, the at least one transmit component and/or the at least one receive component comprises movement toward or away from the target.

13. The method of claim 1, wherein adjusting, from the first detecting position to the second detecting position, the at least one transmit component and/or the at least one receive component comprises movement laterally relative to the target.

14. The method of claim 1, wherein adjusting, from the first detecting position to the second detecting position, the at least one transmit component and/or the at least one receive component comprises a change in shape of the at least one transmit component and/or a change in shape of the at least one receive component.

15. A method of detection of an analyte in a target using a non-invasive analyte sensor, comprising:
with at least one transmit component of the non-invasive analyte sensor and/or at least one receive component of the non-invasive analyte sensor at a first detecting position, transmitting a first transmit signal that is in a radio or microwave frequency range of the electromagnetic spectrum into the target containing the analyte using at least one transmit antenna and detecting a first response, using at least one receive antenna, that results from transmission of the first transmit signal into the target;
adjusting, from the first detecting position to a second detecting position, the at least one transmit component and/or the at least one receive component;
with the at least one transmit component and/or the at least one receive component at the second detecting position, transmitting a second transmit signal that is in a radio or microwave frequency range of the electromagnetic spectrum into the target using the at least one transmit antenna and detecting a second response, using the at least one receive antenna, that results from transmission of the second transmit signal into the target.

16. The method of claim 15, comprising adjusting, from the first detecting position to the second detecting position, the at least one transmit component and the at least one receive component.

17. The method of claim 15, comprising adjusting, from the first detecting position to the second detecting position, the at least one transmit component, and the at least one transmit component comprises the at least one transmit antenna.

18. The method of claim 17, wherein adjusting, from the first detecting position to the second detecting position, the at least one transmit antenna comprises adjusting an angle of the at least one transmit antenna.

19. The method of claim 15, further including at least one transmit signal reflector that reflects the transmit signal from the at least one transmit antenna; and adjusting, from the first detecting position to the second detecting position, the at least one transmit component, and the at least one transmit component comprises the at least one transmit signal reflector.

20. The method of claim 19, wherein adjusting, from the first detecting position to the second detecting position, the at least one transmit signal reflector comprises adjusting an angle of the at least one transmit signal reflector.

21. The method of claim 15, adjusting, from the first detecting position to the second detecting position, the at least one receive component, and the at least one receive component comprises the at least one receive antenna.

22. The method of claim 21, wherein adjusting, from the first detecting position to the second detecting position, the at least one receive antenna comprises adjusting an angle of the at least one receive antenna.

23. The method of claim 15, further comprising at least one receive signal reflector that reflects the response toward the at least one receive antenna; and adjusting, from the first detecting position the second detecting position, the at least one receive component, and the at least one receive component comprises the at least one receive signal reflector.

24. The method of claim 23, wherein adjusting, from the first detecting position to the second detecting position, the at least one receive signal reflector comprises adjusting an angle of the at least one receive signal reflector.

25. The method of claim 15, wherein adjusting, from the first detecting position to the second detecting position, the at least one transmit component and/or the at least one receive component comprises movement toward or away from the target.

26. The method of claim 15, wherein adjusting, from the first detecting position to the second detecting position, the at least one transmit component and/or the at least one receive component comprises movement laterally relative to the target.

27. The method of claim 15, wherein adjusting, from the first detecting position to the second detecting position, the at least one transmit component and/or the at least one receive component comprises a change in shape of the at least one transmit component and/or a change in shape of the at least one receive component.

* * * * *